(12) United States Patent
Rezai et al.

(10) Patent No.: US 11,850,427 B2
(45) Date of Patent: Dec. 26, 2023

(54) METHODS AND SYSTEMS OF IMPROVING AND MONITORING ADDICTION USING CUE REACTIVITY

(71) Applicant: West Virginia University Board of Governors on behalf of West Virginia University, Morgantown, WV (US)

(72) Inventors: Ali Rezai, Morgantown, WV (US); Victor Finomore, Morgantown, WV (US); James Mahoney, Morgantown, WV (US)

(73) Assignee: WEST VIRGINIA UNIVERSITY BOARD OF GOVERNORS ON BEHALF OF WEST VIRGINIA UNIVERSITY, Morgantown, WV (US)

( * ) Notice: Subject to any disclaimer, the term of this patent is extended or adjusted under 35 U.S.C. 154(b) by 382 days.

(21) Appl. No.: 17/110,174

(22) Filed: Dec. 2, 2020

(65) Prior Publication Data
US 2021/0162217 A1 Jun. 3, 2021

Related U.S. Application Data

(60) Provisional application No. 62/942,340, filed on Dec. 2, 2019.

(51) Int. Cl.
| | |
|---|---|
| *A61N 1/36* | (2006.01) |
| *A61N 1/05* | (2006.01) |
| *A61N 2/00* | (2006.01) |
| *G16H 50/30* | (2018.01) |
| *G16H 20/40* | (2018.01) |

(Continued)

(52) U.S. Cl.
CPC ....... *A61N 1/36089* (2013.01); *A61N 1/0534* (2013.01); *A61N 2/002* (2013.01); *A61N 2/006* (2013.01); *A61N 7/00* (2013.01); *G16H 20/40* (2018.01); *G16H 20/70* (2018.01); *G16H 50/30* (2018.01); *A61N 2007/0026* (2013.01)

(58) Field of Classification Search
CPC .. A61N 1/36089; A61N 1/0534; A61N 2/002; A61N 2/006; A61N 7/00; A61N 2007/0026; A61N 1/36139; A61N 1/37258; G16H 20/40; G16H 20/70; G16H 50/30; G16H 20/10; G16H 20/30; G16H 50/20; A61B 5/16
See application file for complete search history.

(56) References Cited

U.S. PATENT DOCUMENTS

| | | | |
|---|---|---|---|
| 10,035,027 | B2 | 7/2018 | Deisseroth et al. |
| 10,232,115 | B2 | 3/2019 | Osorio |

(Continued)

FOREIGN PATENT DOCUMENTS

| | | |
|---|---|---|
| WO | 2015/192189 A1 | 12/2015 |
| WO | 2020/198686 A1 | 10/2020 |
| WO | 2023/278199 A1 | 1/2023 |

*Primary Examiner* — Mark W. Bockelman
(74) *Attorney, Agent, or Firm* — TAROLLI, SUNDHEIM, COVELL & TUMMINO L.L.P.

(57) ABSTRACT

Methods of improving addiction in a patient in need thereof are provided. Methods include exposing the patient to drug related cues and measuring the patient's craving levels or physiological levels during or after cue exposure to determine the patient's status or condition. Such a determination can indicate whether the patient is at risk of engaging in the addictive activity and can guide therapeutic intervention.

18 Claims, 6 Drawing Sheets

(51) Int. Cl.
*G16H 20/70* (2018.01)
*A61N 7/00* (2006.01)

(56) References Cited

U.S. PATENT DOCUMENTS

| | | | |
|---|---|---|---|
| 10,383,571 B1 | 8/2019 | Pulliam et al. |
| 2004/0049134 A1 | 3/2004 | Tosaya et al. |
| 2005/0020945 A1 | 1/2005 | Tosaya et al. |
| 2009/0112133 A1 | 4/2009 | Deisseroth et al. |
| 2011/0112394 A1 | 5/2011 | Mishelevich |
| 2011/0178442 A1 | 7/2011 | Mishelevich |
| 2012/0245493 A1 | 9/2012 | Mishelevich |
| 2012/0283502 A1 | 11/2012 | Mishelevich et al. |
| 2012/0283604 A1 | 11/2012 | Mishelevich |
| 2012/0296241 A1 | 11/2012 | Mishelevich |
| 2013/0079682 A1 | 3/2013 | Mischelevich |
| 2013/0144192 A1 | 6/2013 | Mischelevich et al. |
| 2013/0184728 A1 | 7/2013 | Mishelevich |
| 2013/0197401 A1 | 8/2013 | Sato et al. |
| 2013/0261506 A1 | 10/2013 | Mishelevich |
| 2013/0281890 A1 | 10/2013 | Mishelevich |
| 2014/0094720 A1 | 4/2014 | Tyler |
| 2014/0194726 A1 | 7/2014 | Mishelevich et al. |
| 2015/0025352 A1* | 1/2015 | Caytak ............... A61B 5/0531 600/383 |
| 2015/0182756 A1 | 7/2015 | Peyman |
| 2016/0001096 A1 | 1/2016 | Mishelevich |
| 2016/0243381 A1 | 8/2016 | Alford et al. |
| 2017/0246481 A1 | 8/2017 | Mishelevich |
| 2018/0126191 A1 | 5/2018 | Loike et al. |
| 2018/0140871 A1 | 5/2018 | Konofagou et al. |
| 2018/0214716 A1 | 8/2018 | Goetz et al. |
| 2020/0289855 A1 | 9/2020 | Shimokawa et al. |
| 2021/0138276 A9 | 5/2021 | Kabrams et al. |
| 2022/0168445 A1 | 6/2022 | Kaplitt et al. |

\* cited by examiner

METHODS AND SYSTEMS OF IMPROVING AND MONITORING ADDICTION USING CUE REACTIVITY

CROSS REFERENCE TO RELATED APPLICATIONS

This application claims priority to U.S. Provisional Application No. 62/942,340, filed on Dec. 2, 2019. The entirety of this application is hereby incorporated by reference for all purposes.

GOVERNMENT SUPPORT CLAUSE

This invention was made with government support under grant number DA047714 awarded by the National Institute of Health. The government has certain rights in the invention.

TECHNICAL FIELD

The present disclosure relates to systems and methods of improving and monitoring addiction to an addictive behavior or an addictive chemical substance based on the patient's response to cues associated with the addictive behavior or addictive chemical substance.

BACKGROUND

Nationally, it was estimated that 10.5 million people in the United States (U.S.) misused opioids in 2019. Opioid overdoses in the U.S. have quadrupled since 2000, contributing to over 46,800 overdose deaths in 2018 and accounting for nearly 70% of all drug overdose deaths. The toll of this opioid epidemic goes well beyond overdose survivals and deaths. For example, there has been an upsurge of intravenous drug use resulting in significant increases in infectious diseases. Rates of hepatitis C (HCV) have steadily increased over the past decade. Future generations may be affected as the number of pregnant women with HCV has doubled in recent years and this virus may be transmitted by a pregnant woman to her infant. The morbidity and mortality secondary to the opioid epidemic is currently a significant public health problem.

Although medication-assisted treatment (MAT) has been effective in improving outcomes (abstinence and harm reduction), current opioid use disorder (OUD) treatment is not ideal as approximately 50% of those seeking treatment relapse to opioids and/or other substances. In a multisite, randomized trial, it was reported that the rate of unsuccessful outcomes following MAT (using buprenorphine-naloxone) exceeded 90% and, even when individuals were stabilized on MAT over 12 weeks, the rate of successful outcomes was less than 50%. It has also been reported that many patients never even start the MAT because of withdrawal symptoms, and those who start often discontinue. In addition, patients following MAT can have high relapse rates. Furthermore, many patients with OUD are also using or misusing other addictive substances such as, for example, benzodiazepines, *cannabis*, or cocaine.

Given the current opioid epidemic, the high rate of relapse and overdose deaths, and the additive impact of polysubstance use, it is important to identify new modalities for treating OUD. While we are clearly in the midst of an opioid epidemic, there is also a detrimental impact of other illicit substance use co-occurring in those with OUD. Thus polysubstance use is also a concern suggesting that comprehensive substance use disorder (SUD) prevention and treatment strategies are needed.

SUMMARY

In an aspect, the present disclosure provides a method of improving addiction to an addictive behavior or addictive chemical substance in a patient in need thereof comprising obtaining a measurement of the patient's baseline craving level for the addictive behavior or addictive chemical substance. The method further includes providing the patient exposure to a cue associated with the addictive behavior or addictive chemical substance. The method further comprises obtaining a subsequent measurement of the patient's resultant craving level for the addictive behavior or addictive chemical substance during or after exposure to the cue. The method additionally comprises providing or adjusting therapy to the patient based on a comparison of the baseline craving level and the resultant craving level to improve the patient's addiction.

In another aspect, the present disclosure provides a method of improving addiction to an addictive behavior or addictive chemical substance in a patient in need thereof comprising obtaining a measurement of a baseline value of a physiological, cognitive, psychosocial, or behavioral parameter of the patient and providing the patient exposure to a cue associated with the addictive behavior or addictive chemical substance. The method further includes obtaining a subsequent measurement of a resultant value of the physiological, cognitive, psychosocial, or behavioral parameter during or after exposure to the cue. The method additionally comprises providing or adjusting therapy to the patient based on a comparison of the baseline value and the resultant value to improve the patient's addiction.

In another aspect, the present disclosure provides a method of monitoring addiction to an addictive behavior or addictive chemical substance in a patient in need thereof comprising obtaining a measurement of a baseline value of a physiological, cognitive, psychosocial, or behavioral parameter of the patient or a baseline craving level of the patient. The method further comprises providing the patient exposure to a cue associated with the addictive behavior or addictive chemical substance and obtaining a measurement of a resultant value of the physiological, cognitive, psychosocial, or behavioral parameter or a resultant craving level during or after exposure to the cue. The method also includes obtaining a comparison of the resultant physiological, cognitive, psychosocial, or behavioral value and the baseline value or a comparison of the resultant craving level and the baseline craving level and providing a notification to the patient or a third party based on the comparison of the baseline values and the resultant values or the baseline craving level and the resultant craving level to monitor the patient's addiction.

DETAILED DESCRIPTION

As used herein with respect to a described element, the terms "a," "an," and "the" include at least one or more of the described element including combinations thereof unless otherwise indicated. Further, the terms "or" and "and" refer to "and/or" and combinations thereof unless otherwise indicated. The term "based on" means based at least in part on. Additionally, where the disclosure or claims recite "a," "an," "a first," or "another" element, or the equivalent thereof, it should be interpreted to include one or more than one such element, neither requiring nor excluding two or more such elements.

The present disclosure relates to improving addiction to an addictive behavior or addictive chemical substance in a patient who is suffering from such addiction and is in need of therapy. By improving addiction, the patient's addiction is less severe after therapy than before therapy. For example, the patient's addiction can be improved by reducing the patient's craving. If craving is reduced, this can contribute to improvements in the patient's mood and anxiety as well as improvements in cognitive aspects such as executive function and impulse control. The patient's addiction cycle can also be improved including use, misuse and addiction.

Methods as disclosed herein can involve measuring baseline craving levels and/or baseline physiological, cognitive, psychosocial, behavioral parameter values, or combinations thereof (also referred to herein as "baseline parameter values") and comparing these baseline craving levels or baseline parameter values measured during or after a patient is exposed to a drug-related cue (also referred to herein as "resultant craving levels" or "resultant parameter values"). The patient's response to these drug-related cues can serve as feedback parameters or predictive markers of relapse to aid the clinician in monitoring the patient's status and condition and to provide or adjust therapy accordingly. As such, the craving levels and physiological, cognitive, psychosocial, or behavioral parameter values after cue exposure can effectively gauge the patient's impulsivity, self-regulation, decision making and other functions related to addiction or relapse so that a clinician can determine the patient's risk of engaging in addictive behavior or consuming an addictive chemical substance such that the clinician potentially can provide intervening therapy before the patient engages in such behavior or consumption.

Figure 1:
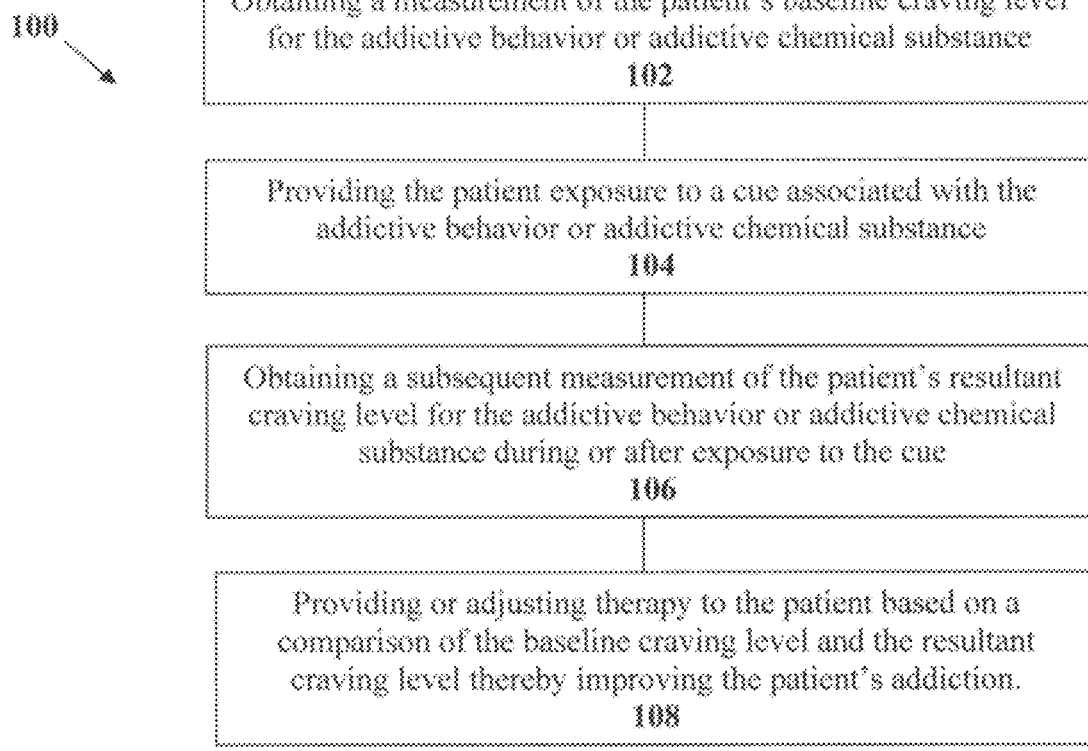
FIG. 1 is a flow diagram outlining steps of a method of improving addiction according to an aspect of the present disclosure.

Referring to FIG. 1, in an aspect, a method of improving addiction to an addictive behavior or an addictive chemical substance in a patient in need thereof 100 can comprise obtaining a measurement of the patient's baseline craving level for the addictive behavior or the addictive chemical substance 102. These baseline levels, which can be taken at various time points before or during therapy, can be taken while the patient is under a standard of care for addiction as outlined, for example, by the American Society of Addiction Medicine (ASAM 2013). These baseline levels can be taken at intake, during the course of medicated assisted, and/or behavioral treatment. Such baseline craving levels can be measured in a clinical/laboratory setting. Craving can be assessed, for example, by asking the patient to rate his or her craving to the substance or behavior for which the patient is seeking therapy via a 100-point visual analog scale (VAS) where 100 represents maximum craving and 0 represents no craving. After this initial craving assessment, method 100 can comprise exposing the patient to a cue associated with the addictive behavior or addictive chemical substance 104 followed by an assessment of the patient resultant craving level to determine changes in craving during or following cue exposure. The patient's resultant or subsequent craving level is measured proximate in time during or after exposure to the cue such that the patient's resultant craving level correlates to the patient's response to the cue. For example, the resultant craving level can be measured during exposure to the cue, within five minutes after exposure to the cue, within ten minutes after exposure to the cue, or any measurable time periods therebetween. More specifically, method 100 can comprise obtaining a measurement of the resultant patient's craving level for the addictive behavior or addictive chemical substance proximate in time during or after exposure to the cue 106 and determining if there is an increase in the patient's resultant craving level or if the patient's resultant craving level remains substantially the same as the baseline craving level. Method 100 can then comprise providing or adjusting therapy based on a comparison of the baseline craving level and the resultant craving level to improve the patient's addiction 108. For example, therapy can be provided or adjusted upon a determination that the resultant craving level increases above the patient's baseline craving level.

Figure 2:
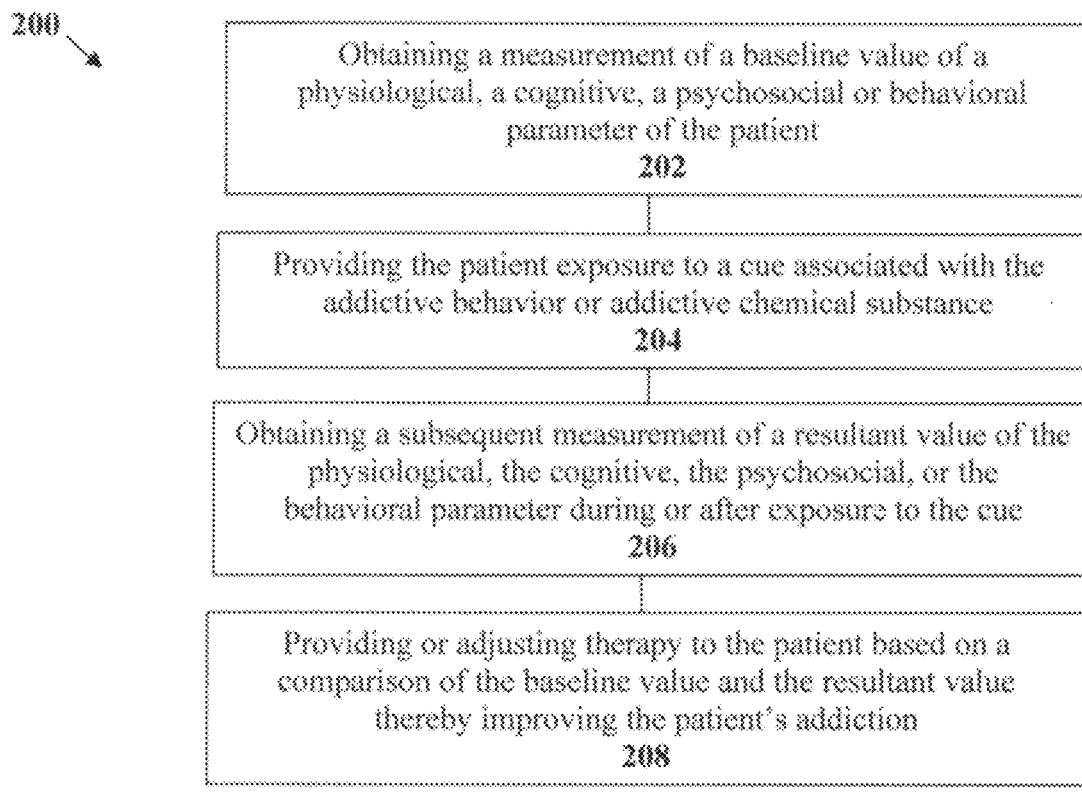
FIG. 2 is a flow diagram outlining steps of a method of improving addiction according to another aspect of the present disclosure.

Referring to FIG. 2, in another aspect a method of improving addiction to an addictive behavior or an addictive chemical substance in a patient in need thereof 200 can comprise obtaining a measurement of a baseline value of a physiological, cognitive, psychosocial, or behavioral parameter of the patient 202. These baseline values, which can be taken at various time points before or during therapy, can be taken while the patient is under a standard of care for addiction as outlined, for example, by the American Society of Addiction Medicine (ASAM 2013). These baseline parameter values can be taken at intake, during the course of medicated assisted, and/or behavioral treatment. Such baseline parameter values can be taken in or outside of a clinical/laboratory setting. After this initial assessment, method 200 can comprise exposing the patient to a cue associated with the addictive behavior or the addictive chemical substance 204 followed by an assessment of the patient's resultant parameter value to determine changes in the parameter value during or following cue exposure. The patient's resultant or subsequent parameter value is measured proximate in time during or after exposure to the cue such that the patient's resultant parameter measurement value correlates to the patient's response to the cue. For example, the resultant parameter value can be measured during exposure to the cue, within five minutes after exposure to the cue, within ten minutes after exposure to the cue, or any measurable time periods therebetween. More specifically, method 200 can comprise obtaining a measurement of a resultant value of the parameter proximate in time during or after exposure to the cue 206 to determine if there is an increase in the resultant value of the parameter or if the resultant parameter value remains substantially the same as the baseline parameter value. Method 200 can then comprise providing or adjusting therapy to the patient based on a comparison of the resultant parameter value and the baseline parameter value to improve the patient's addiction 208. For example, therapy can be provided or adjusted based upon a determination that the resultant parameter value increases above the patient's baseline parameter value.

Figure 3:
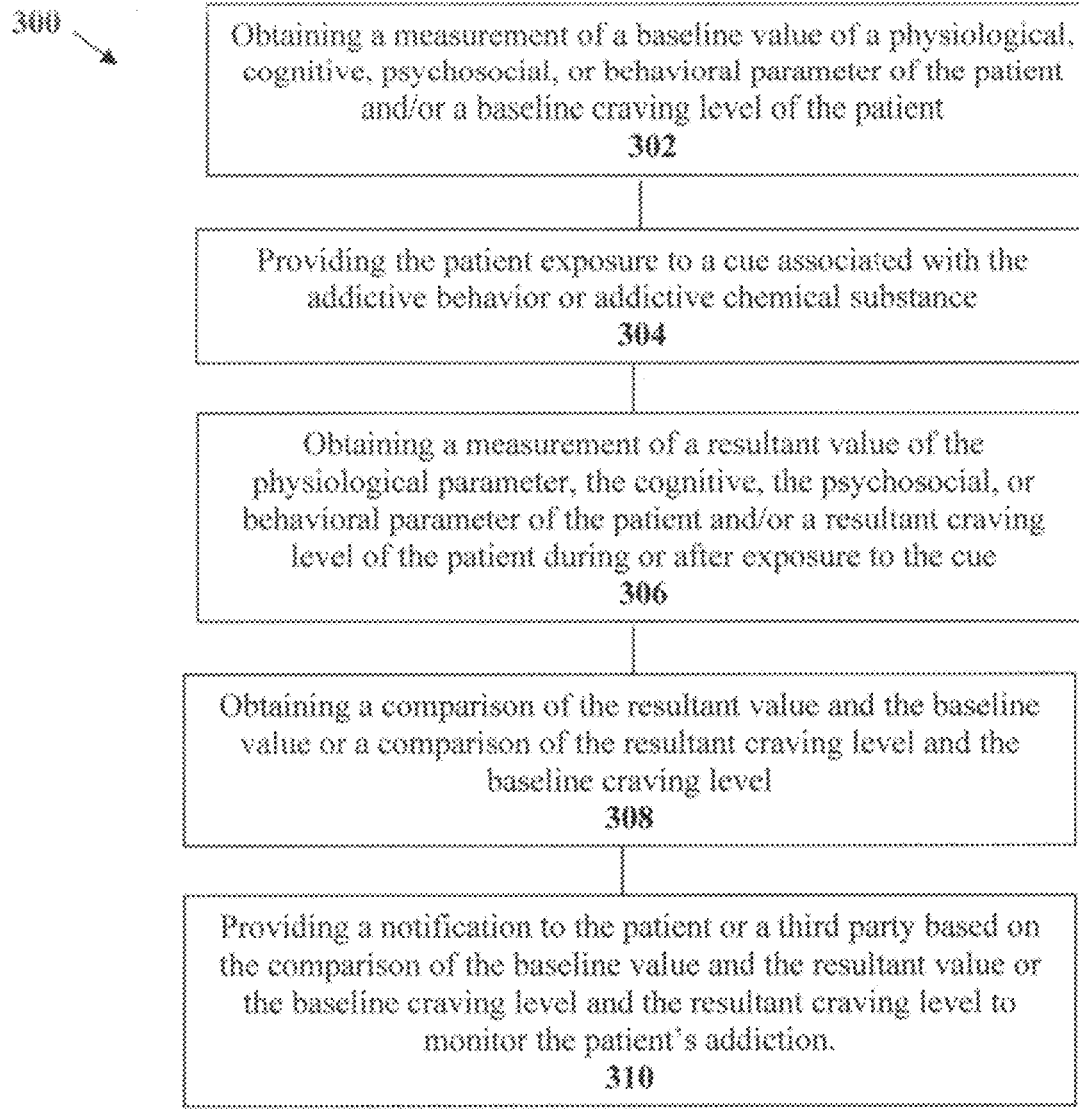
FIG. 3 is a flow diagram outlining steps of a method of improving addiction according to another aspect of the present disclosure.
Figure 4:
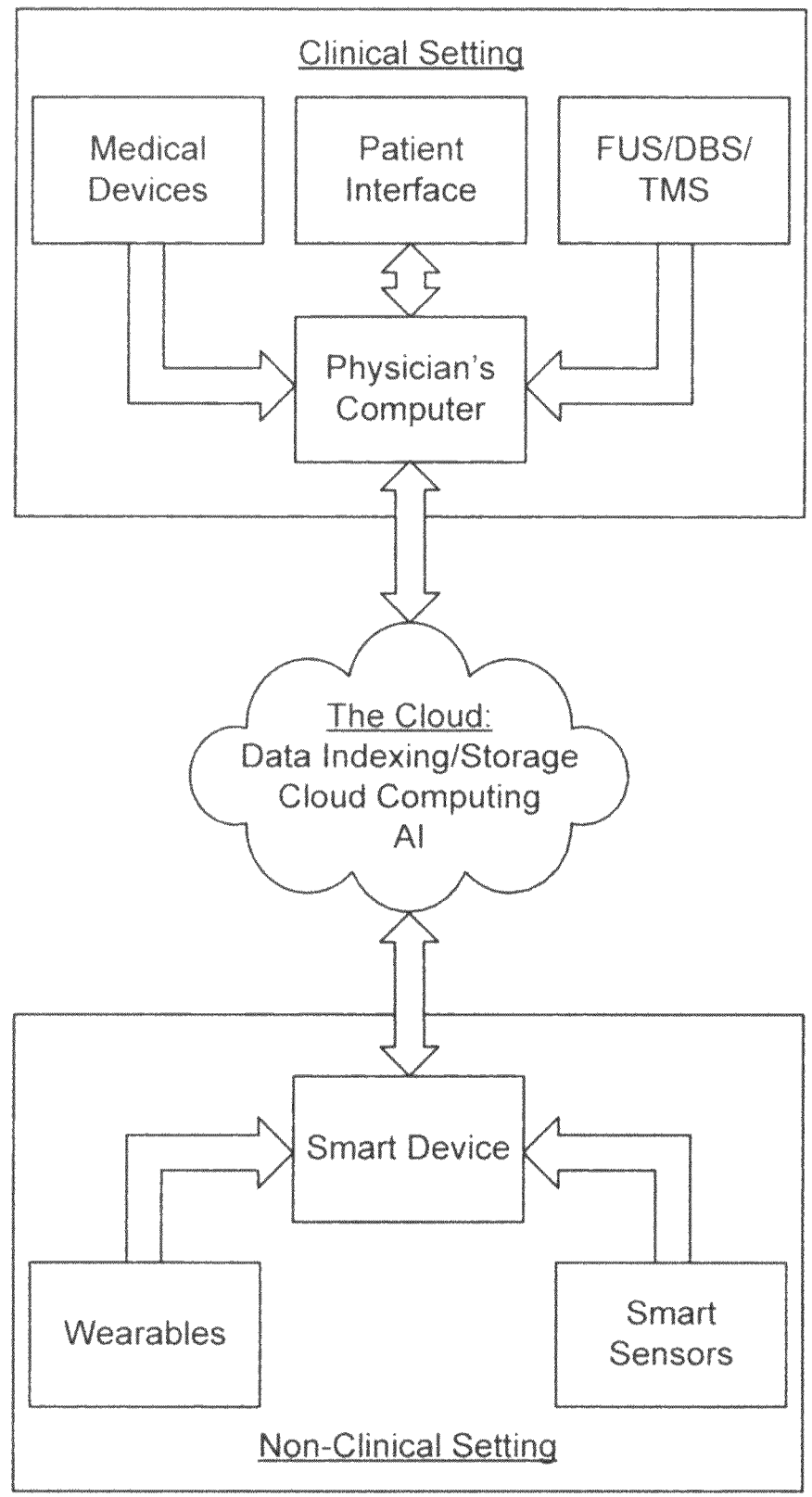
FIG. 4 is block diagram of a system according to an aspect of the present disclosure.

The present disclosure also provides a method of monitoring a patient's addiction. Referring to FIG. 3, in an aspect, a method of monitoring addiction to an addictive behavior or an addictive chemical substance in a patient in need thereof 300 can comprise obtaining a measurement of a baseline value of a physiological, cognitive, psychosocial, or behavioral parameter of the patient and/or a baseline craving level of the patient 302. This baseline parameter value or baseline craving level, which can be taken at various time points before or during therapy, can be taken while the patient is under a standard of care for addiction as outlined, for example, by the American Society of Addiction Medicine (ASAM 2013). These baseline parameter values and baseline craving levels can be taken at intake, during the course of medicated assisted, and/or behavioral treatment. Such baseline parameter value or baseline craving level can be taken in or outside a clinical/laboratory setting. After this initial physiological, cognitive, psychosocial, behavioral or craving assessment, method 300 can comprise exposing the patient to a cue associated with the addictive behavior or addictive chemical substance 304 followed by an assessment of the patient's parameter value or craving level to determine changes in the resultant parameter value or resultant craving level during or following cue exposure. As stated above, the patient's resultant or subsequent parameter value or craving level is measured proximate in time during or after exposure to the cue such that the patient's resultant parameter measurement value or resultant craving level correlates to the patient's response to the cue. For example, the resultant parameter value or resultant craving level can be measured during exposure to the cue, within five minutes after exposure to the cue, within ten minutes after exposure to the cue, or any measurable time periods therebetween. More specifically, method 300 can comprise obtaining a measurement through data analytics and machine learning approaches of a resultant value of the parameter or a resultant craving level proximate in time during or after exposure to the cue 306 and obtaining a comparison of the resultant parameter value and the baseline parameter value or the resultant craving level and the baseline craving level to determine if there is increase in the resultant value of the parameter or the resultant craving level or if the resultant parameter value or the resultant craving level remains substantially the same as the baseline parameter value or baseline parameter craving level 308. Method 300 can then comprise providing a notification to the patient or a third party based on the comparison of the baseline parameter value and the resultant parameter value or the comparison of the baseline craving level and the resultant craving level to monitor the patient's addiction 310. For example, the patient or a third party can be notified upon a determination that the resultant parameter value or resultant craving level increases above the patient's baseline parameter value or baseline craving level.

The cue to which the patient is exposed can be a visual cue, an auditory cue, a tactile cue, an olfactory cue, or combinations thereof. The patient can be exposed to the cues via a smart phone, tablet, personal computer or laptop, for example, in a naturalistic non-clinical setting such as when the patient is at home, work or other non-clinical setting. The patient can be exposed to the cues via virtual reality, augmented reality, or mixed reality. The patient can be exposed to multiple cues during any assessment period and, in the case of polysubstance use or behavior, the patient can be exposed to cue associated with the different addictive substances or behaviors. In the case of addiction to a chemical substance, the cue can be, for example, images of drugs, drug paraphernalia, or individuals using drugs. The cue can be specific for the particular addictive behavior or addictive chemical substance for which the patient is seeking therapy and can include multiple cues, including multiple different types of cues. For example, if the patient is addicted to alcohol, the cue can be the scent of alcohol, a visual image of a bar, or the sound of an alcoholic beverage container being opened. If the patient is addicted to heroin, the cues can be visual images of heroin, a hypodermic needle, or a spoon and lighter, for example. If the patient is addicted to gambling, the cue can be a visual image of a casino or gambling chips, for example. The above examples are only exemplary and are meant to point out that the cues can be addiction specific and can stimulate different senses. The cues can also be similar to the patient's characteristics such as, for example, the patient's age, gender, ethnicity, preferred chemical substances and routes of administration. In other words, the cues to which the patient is exposed can be personalized to the specific patient seeking therapy.

In aspects where a patient's physiological parameter is measured, the physiological parameter can be a response of the patient's autonomic nervous system to cue exposure and multiple physiological parameters can be measured during any given assessment session. The physiological parameters can be measured via a wearable device such as a ring, watch, or belt or via a smart phone or tablet, for example, in a naturalistic non-clinical setting such as when the patient is at home, work or other non-clinical setting. Exemplary physiological parameters include heart rate, heart rate variability, perspiration, salivation, blood pressure, pupil size, brain activity, electrodermal activity, body temperature, and blood oxygen saturation level. Table I provides non-limiting examples of physiological parameters that can be measured and exemplary tests to measure the physiological parameters.

TABLE I

| Physiological Parameter | Exemplary Devices and Methods to Measure Physiological Parameters |
| --- | --- |
| Brain Activity | Electroencephalogram, Photoplethysmogram, Magnetic Resonance Imaging including functional Magnetic Resonance Imaging (fMRI) |
| Heart Rate | Electrocardiogram and Photoplethysmogram |
| Heart Rate Variability | Electrocardiogram |
| Eye Tracking including tracking saccades, fixations, and pupil size (e.g. dilation) | Pupillometry |

TABLE I-continued

| Physiological Parameter | Exemplary Devices and Methods to Measure Physiological Parameters |
|---|---|
| Perspiration | Perspiration Sensor |
| Blood Pressure | Sphygmomanometer |
| Body temperature | Thermometer |
| Blood oxygen saturation | Pulse Oximeter |
| Electrodermal Activity | Electrodermal Sensor |
| Autonomic Tone | Derived from above measurements |
| Emotional State | Facial Expression Analysis |
| Daily Movement and Sleep | Accelerometer |

In addition to the above physiological parameters that can provide an objective numerical value once measured, methods can also include obtaining facial expression analysis in order to provide insight into the patient's emotional state. If the facial expression analysis indicates facial expressions indicative of anxiety or agitation, this can indicate that the patient is craving the addictive behavior or addictive chemical substance.

As stated above, aspects of the present disclosure include obtaining a measurement of a baseline value of a physiological parameter of the patient or a baseline craving level, obtaining a measurement of a resultant value of the physiological parameter or resultant craving level proximate in time to exposure to a cue associated with the addictive behavior or addictive chemical substance, and determining changes in the resultant value or resultant craving level compared to the baseline value or baseline level. The baseline and resultant values and levels can be stored in a data storage and processing unit and the comparison between the resultant values and levels and the baseline values and levels can be performed by the data storage and processing unit that receives all the baseline values and levels and resultant values and levels and executes steps to process and index such data.

In the context of physiological parameter values and determining changes in such values, methods can involve, for example, determining whether the patient's brain activity, heart rate, heart rate variability, pupil size, perspiration, blood pressure, body temperature, blood oxygen saturation level, or electrodermal activity increases after exposure to the cue. If the value of such parameters increases, this can be an indication that the patient may be at risk of engaging in the addictive behavior or consuming the addictive chemical substance. Conversely, if the value of such parameters is substantially the same as the baseline value, this can indicate that the patient is stable or is not at risk of engaging in addictive behavior or consuming the addictive chemical substance such that intervention or therapy may not be necessary.

The cognitive parameters can be assessed by a battery of cognitive tests that measure, for example, executive function, decision making, working memory, attention, and fatigue. Table II provides non-limiting examples of cognitive parameters that are gamified and that can be measured and exemplary methods and tests/tasks to measure such cognitive parameters.

TABLE II

| Cognitive Parameter | Exemplary Tests and Methods to Measure Cognitive Parameters |
|---|---|
| Temporal discounting | Kirby Delay Discounting Task |
| Alertness and fatigue | Psychomotor Vigilance Task |
| Focused attention and response inhibition | Erikson Flanker Task |
| Working memory | N-Back Task, Digit span, number letter sequencing |
| Attentional bias towards emotional cues | Dot-Probe Task |
| Inflexible persistence | Wisconsin Card Sorting Task |
| Decision making | Iowa Gambling Task |
| Risk taking behavior | Balloon Analogue Risk Task |
| Inhibitory control | Anti-Saccade Task |
| Sustained attention | Sustained Attention |
| Executive function | Task Shifting or Set Shifting Task, trail making |

These cognitive tests can be administered in a clinical/laboratory setting or in a naturalistic, non-clinical setting such as when the user is at home, work or other non-clinical setting. A smart device, such as a smartphone, tablet, or smart watch, can facilitate measuring these cognitive parameters in a naturalistic, non-clinical setting. For example, the Erikson Flanker, N-Back and Psychomotor Vigilance Tasks can be taken via an application on a smart phone, tablet, or smart watch.

Table III provides non-limiting examples of psychosocial and behavioral parameters that can be measured and exemplary tests, devices, and methods, to measure the behavioral parameters.

TABLE III

| Psychosocial or Behavioral Parameter | Exemplary Tests and Methods to Measure Psychosocial or Behavioral Parameters |
| --- | --- |
| Burnout | Burnout inventory or similar |
| Physical, Mental, and Social Health | User-Reported Outcomes Measurement Information System (PROMIS), Quality of Life SF-36 |
| Depression | Hamilton Depression Rating Scale |
| Anxiety | Hamilton Anxiety Rating Scale |
| Mania | Snaith-Hamilton Pleasure Scale, Young Mania Rating scale |
| Mood/ Catastrophizing scale | Profile of Mood States; Positive Affect Negative Affect Schedule |
| Affect | Positive Affect Negative Affect Schedule |
| Impulsivity | Barratt Impulsiveness Scale |
| Anhedonia | Snaith-Hamilton Pleasure Scale |
| Sleep | Sleep onset & offset, sleep quality, sleep quantity, from wearable accelerometer and PPG |
| Activity level | Daily movement total, time of activities, from wearable accelerometer, steps |

The behavioral and psychosocial parameters can measure the user's functionality, such as the user's movement via wearable devices as well as subjective/self-reporting questionnaires. The subjective/self-reporting questionnaires can be collected in a clinical/laboratory setting or in a naturalistic, in the wild, non-clinical setting such as when the user is at home, work, or other non-clinical setting. A smart device, such as a smartphone, tablet, or personal computer can be used to administer the subjective/self-reporting questionnaires. Using embedded accelerometers and cameras, these smart devices can also be used to capture the user's movements as well as facial expression analysis to analyze the user's facial expressions that could indicate mood, anxiety, depression, agitation, and fatigue.

In addition to one or more combinations of physiological, cognitive, psychosocial, and behavioral parameters, clinical data can also be part of the multi-dimensional feedback approach to predicting craving level. Such clinical data can include, for example, the user's clinical state, the user's medical history (including family history), employment information, and residential status.

In certain aspects, once an assessment has been made as to whether the patient's physiological, cognitive, psychosocial, or behavioral parameter measurement values or craving levels change after cue exposure, a method can involve providing or adjusting therapy to the patient to improve the patient's addiction. Such therapy can include, for example, different forms of neuromodulation. Neuromodulation generally involves altering nerve activity through targeted delivery of a stimulus, such as electrical stimulation or chemical agents, to specific neurological sites in the body. Non-limiting examples of stimulus or forms of energy that can be delivered to a neural target site of the patient include electrical, ultrasound or acoustic, magnetic, optical, and chemical stimuli. In certain aspects, the neuromodulation is focused ultrasound (FUS). In other aspects, the neuromodulation is transcranial magnetic stimulation (TMS). In still other aspects, the neuromodulation is deep brain stimulation (DBS). The neural target site to which the stimulus is delivered can be a component of the patient's reward circuitry, such as, the nucleus accumbens, the striatum including the ventral and dorsal striatum, the insula, the anterior cingulate cortex, the prefrontal cortex including the dorsolateral prefrontal cortex, the hippocampus, the amygdala, or combinations thereof. The stimulus can be applied to a neural target site unilaterally or bilaterally. Table II provides an exemplary list of neural target sites, exemplary forms of neuromodulation, and exemplary neuromodulation parameters parameters that can be applied to these neural target sites as part of the patient's therapy.

TABLE II

| Exemplary Target Site | Exemplary Form of Neuromodulation | Exemplary Neuromodulation Parameters |
| --- | --- | --- |
| Nucleus Accumbens | DBS and FUS | DBS parameters: frequency of ~1 Hz to ~10,000 Hz; pulse width of ~5 microseconds to ~1000 microseconds; intensity of ~0.1 v or mA to ~30 v or mA FUS parameters: sonication dose; power (~0 W-~150 W); sonication duration (~0 min-~30 min to ~60 min); frequency direction, repetition time on/off (5 sec; 10 sec), pulse duration on/off (100 msec; 900 msec), continuous or burst; energy/minute (~0 J/min-~290 J/min; frequency (~.1-~3 MHz); and number of elements (~1-~1024). |
| Striatum including dorsal striatum, ventral striatum, and ventral capsule | DBS and FUS | DBS parameters: frequency of ~1 Hz to ~10,000 Hz; pulse width of ~5 microseconds to ~1000 microseconds; intensity of ~0.1 v or mA to ~30 v or mA FUS parameters: sonication dose; power (~0 W-~150 W); sonication duration (~0 min-~30 min to ~60 min); frequency direction, repetition time on/off (5 sec; 10 sec), pulse duration on/off (100 msec; 900 msec), continuous or burst; energy/minute (~0 J/min-~290 J/min; frequency (~.1-~3 MHz); and number of elements (~1-~1024) |
| Insula | TMS, DBS and FUS | TMS parameters: intensity (~0-~200% resting motor threshold); frequency (~.01 Hz-~30 Hz); type of stimulation (single, repetitive, patterned), and duration (~1-~90 min) DBS parameters: frequency of ~1 Hz to ~10,000 Hz; pulse width of ~5 microseconds to ~1000 microseconds; intensity of ~0.1 v or mA to ~30 v or mA FUS parameters: sonication dose; power (~0 W-~150 W); sonication duration (~0 min-~30 min to ~60 min); frequency direction, repetition time on/off (5 sec; 10 sec), pulse duration on/off (100 msec; 900 msec), continuous or burst; energy/minute (~0 J/min-~290 J/min; frequency (~.1-~3 MHz); and number of elements (~1-~1024) |
| Anterior Cingulate Cortex | TMS, DBS and FUS | TMS parameters: intensity (~0-~200% resting motor threshold); frequency (~.01 Hz-~30 Hz); type of stimulation (single, repetitive, patterned), and duration (~1-~90 min) DBS parameters: frequency of ~1 Hz to ~10,000 Hz; pulse width of ~5 microseconds to ~1000 microseconds; intensity of ~0.1 v or mA to ~30 v or mA FUS parameters: sonication dose; power (~0 W-~150 W); sonication duration (~0 min-~30 min to ~60 min); frequency direction, repetition time on/off (5 sec; 10 sec), pulse duration on/off (100 msec; 900 msec), continuous or burst; energy/minute (~0 J/min-~290 J/min; frequency (~.1-~3 MHz); and number of elements (~1-~1024) |
| Prefrontal Cortex including dorsolateral prefrontal cortex | TMS, DBS and FUS | TMS parameters: intensity (~0-~200% resting motor threshold); frequency (~.01 Hz-~30 Hz); type of stimulation (single, repetitive, patterned), and duration (~1-~90 min) DBS parameters: frequency of ~1 Hz to ~10,000 Hz; pulse width of ~5 microseconds to ~1000 microseconds; intensity of ~0.1 v or mA to ~30 v or mA FUS parameters: sonication dose; power (~0 W-~150 W); sonication duration (~0 min-~30 min to ~60 min); frequency direction, repetition time on/off (5 sec; 10 sec), pulse duration on/off (100 msec; 900 msec), continuous or burst; energy/minute (~0 J/min-~290 J/min; frequency (~.1-~3 MHz); and number of elements (~1-~1024) |
| Hippocampus | DBS and FUS | DBS parameters: frequency of ~1 Hz to ~10,000 Hz; pulse width of ~5 microseconds to ~1000 microseconds; intensity of ~0.1 v or mA to ~30 v or mA FUS parameters: sonication dose; power (~0 W-~150 W); sonication duration (~0 min-~30 min to ~60 min); frequency direction, repetition time on/off (5 sec; 10 sec), pulse duration on/off (100 msec; 900 msec), continuous or burst; energy/minute (~0 J/min-~290 J/min; frequency (~.1-~3 MHz); and number of elements (~1-~1024) |
| Amygdala | DBS and FUS | DBS parameters: frequency of ~1 Hz to ~10,000 Hz; pulse width of ~5 microseconds to ~1000 microseconds; intensity of ~0.1 v or mA to ~30 v or mA FUS parameters: sonication dose; power (~0 W-~150 W); sonication duration (~0 min-~30 min to ~60 |

TABLE II-continued

| Exemplary Target Site | Exemplary Form of Neuromodulation | Exemplary Neuromodulation Parameters |
| --- | --- | --- |
| | | min); frequency direction, repetition time on/off (5 sec; 10 sec), pulse duration on/off (100 msec; 900 msec), continuous or burst; energy/minute (~0 J/min-~290 J/min; frequency (~.1-~3 MHz); and number of elements (~1-~1024) |

The type of change of the patient's physiological parameter measurement values or craving level during or after cue exposure can influence whether therapy is provided or if existing therapy should be adjusted. For example, in terms of providing therapy, if there is an increase in the patient's physiological parameter measurement value or craving level during or after cue exposure compared to the baseline physiological parameter measurement value or baseline craving level, a method can involve initiating neuromodulation. Conversely, if the physiological parameter measurement value or craving level during or after cue exposure is substantially the same as the baseline physiological parameter measurement value or baseline craving level, neuromodulation may not be applied. In terms of adjusting therapy in the context of neuromodulation, methods can involve adjusting the parameters or dosing of the neuromodulation such as, for example, the duration, frequency, or intensity of the neuromodulation. If there is an increase in the patient's physiological parameter measurement value or craving level during or after cue exposure compared to the baseline physiological parameter measurement value or baseline craving level, a method can involve adjusting the neuromodulation so that the neuromodulation is more effective. For example, if the patient was previously having FUS delivered for five minutes during a therapy session, the patient can have the FUS subsequently delivered for twenty minutes during each session or if the patient was having FUS delivered every thirty days, the patient can have FUS subsequently delivered every two weeks. Conversely, if the physiological parameter measurement value or craving level after cue exposure is substantially the same as the baseline physiological parameter measurement value or baseline craving level, the neuromodulation parameters may not need adjustment and subsequent neuromodulation sessions can serve primarily as maintenance sessions or the intensity, frequency or duration of the neuromodulation can be decreased, for example. Alternatively, if the physiological parameter measurement value or craving level during or after cue exposure is substantially the same as the baseline physiological parameter measurement value or baseline craving level, then the patient can stop receiving any subsequent neuromodulation. The above scenarios are only exemplary and are provided to illustrate that the presence and type of change of the patient's physiological parameter measurement values and craving levels during and after cue exposure can influence whether therapy is provided or if existing therapy should be adjusted or terminated.

Further, the degree of the patient's physiological, cognitive, psychosocial, or behavioral parameter measurement value during or after cue exposure as well as the degree of the patient's craving level during or after cue exposure can influence the parameters of initial or subsequent therapy. For example, if the specific patient seeking therapy has a craving level during or after cue exposure that is higher than the average craving level of the same patient population (patients with the same addiction), the therapy can be more aggressive initially or subsequently (e.g. in the context of neuromodulation, the duration, frequency, or intensity of the neuromodulation can be greater than that provided to patients of the same patient population). Similarly, if the specific patient seeking therapy has a physiological, cognitive, psychosocial, or behavioral parameter measurement value during or after cue exposure that is higher than the average parameter measurement value of the same patient population, the therapy can be more aggressive initially or subsequently. Conversely, if the specific patient's craving level or parameter measurement value during or after cue exposure is lower than the average craving level or parameter measurement value of the same patient population, the therapy can be less aggressive initially or subsequently. In other words, the severity or degree of the patient's resultant craving level or resultant physiological, cognitive, psychosocial, or behavioral parameter measurement value during or after cue exposure (as well as baseline values and levels) can correlate to the degree or aggressiveness of the therapy. The above scenarios are only exemplary and are provided to illustrate that the degree of change of the patient's physiological parameter measurement values and craving levels during and after cue exposure can influence the parameters of initial and subsequent therapy.

Providing or adjusting therapy to the patient can include therapies that do not involve a medical procedure. For example, providing therapy can include providing the patient with a list of nearby group therapy sessions or nearby individual counselors. Alternatively, providing therapy can include automatically contacting an addiction counselor or the patient's sponsor. For example, if there is an increase in the patient's parameter measurement value or craving level during or after cue exposure compared to the baseline parameter measurement value or baseline craving level, methods can involve providing these types or non-surgical therapies.

As described above, methods of monitoring a patient's addiction to an addictive behavior or addictive chemical substance are also provided herein. As stated above, such monitoring can include providing a notification to the patient or a third party based on the comparison of the patient's baseline physiological, cognitive, psychosocial, or behavioral parameter measurement value (baseline parameter value) and the patient's physiological, cognitive, psychosocial, or behavioral physiological parameter measurement value during or after exposure to a cue (resultant parameter value) or a comparison of the patient's baseline craving level and the patient's craving level during or after exposure to a cue (resultant craving level). For example, the patient or a third party can be notified upon a determination that the resultant parameter value or resultant craving level increases above the patient's baseline parameter value or baseline craving level. The third party can include a member of the patient's support network, such as a family member, caretaker, a friend, a sponsor, a counselor, or another individual that may be able to intervene before the patient potentially engages in the addictive behavior or consumes the addictive chemical substance. The patient can also be provided with the notification to alert the patient that he or she is at risk of engaging in the addictive behavior or consuming the addictive chemical substance so that the patient can potentially employ self-regulation techniques to avoid relapsing or otherwise seeking assistance.

The third party can also include the patient's clinician such that the clinician can potentially adjust subsequent therapy. The notification can also provide the clinician with the degree of change between the patient's baseline physiological, cognitive, psychosocial, or behavioral value and resultant physiological, cognitive, psychosocial, or behavioral value or baseline craving level and resultant craving level such that, for example, the clinician can categorize the patient's risk level as "high," "medium," or "low" and adjust subsequent therapy accordingly. The data analytics will take baseline and subsequent measurements of physiological, cognitive, psychosocial, or behavioral and craving values and create predictive model for when a user is at greater or lower risk of increased cravings and relapse.

Figure 5:
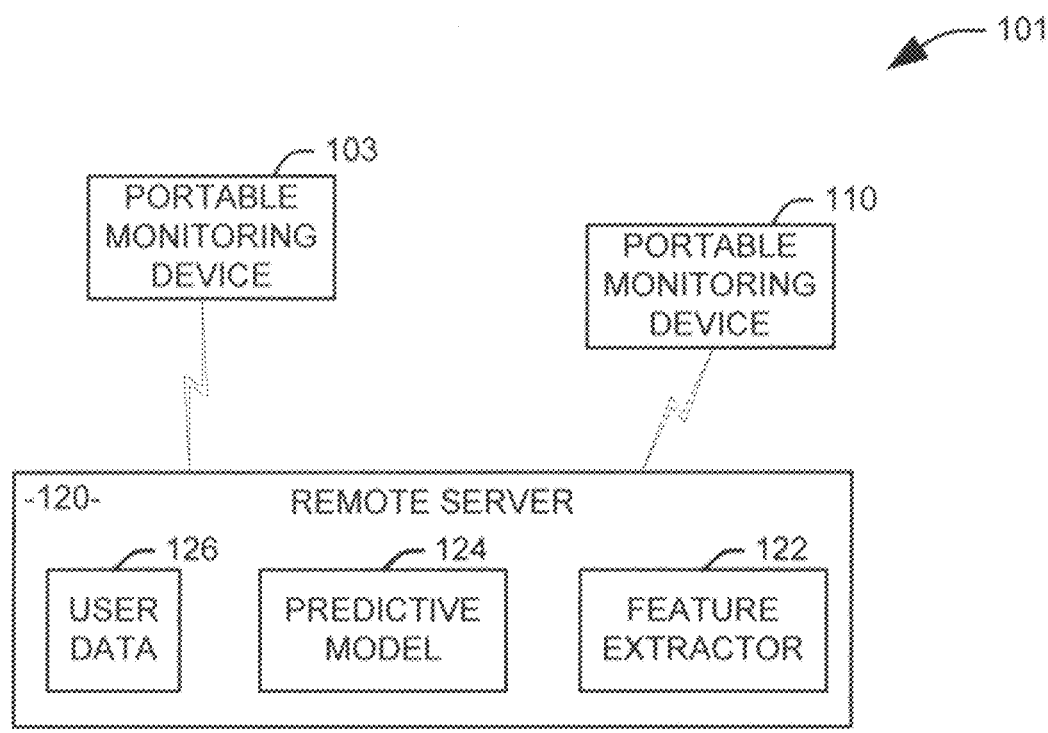
FIG. 5 is a block diagram of a system according to an aspect of the present disclosure.

Referring to FIG. 5, a system 101 can include a remote server 120 that analyzes the data collected by portable monitoring devices 103 and 110. The remote server 120 can be implemented as a dedicated physical server or as part of a cloud server arrangement. In addition to the remote server, data can be analyzed on the local device itself and/or in a federated learning mechanism. Information received from the portable monitoring devices 103 and 110 is provided to a feature extractor 122 that extracts a plurality of features for use at a predictive model 124. The feature extractor 122 determines categorical and continuous parameters representing the craving relevant parameters. In one example, the parameters can include descriptive statistics, such as measures of central tendency (e.g., median, mode, arithmetic mean, or geometric mean) and measures of deviation (e.g., range, interquartile range, variance, standard deviation, etc.) of time series of the monitored parameters, as well as the time series themselves. In one implementation, the feature extractor 124 can perform a wavelet transform on the time series of values for one or more parameters to provide a set of wavelet coefficients. It will be appreciated that the wavelet transform used herein is two-dimensional, such that the coefficients can be envisioned as a two-dimensional array across time and either frequency or scale.

For a given time series of parameters, xi, the wavelet coefficients, Wa(n), produced in a wavelet decomposition can be defined as:

$$W_a(n) = a^{-1} \sum_{i=1}^{M} x_i \Psi\left(\frac{i-n}{a}\right) \quad \text{Eq. 3}$$

wherein ψ is the wavelet function, M is the length of the time series, and a and n define the coefficient computation locations.

Additionally or alternatively, the wellness-relevant parameters can be used to assign a plurality of categorical parameters to the user according to thresholds for craving-relevant parameters or rule sets that act upon time series of values for the craving-relevant parameters, for example, representing the presence or absence of a given condition or behavior. The predictive model 124 can also utilize user data 126 stored at the remote server 120, including, for example, employment information (e.g., title, department, shift), age, sex, home zip code, genomic data, nutritional information, medication intake, household information (e.g., type of home, number and age of residents), social and psychosocial, consumer spending and profiles, financial, food safety, physical abuse, and relevant medical history. In addition the model can combine multiple users to interact together to refine prediction such as social model of spouse, children, family, sponsor, friends and others.

The predictive model 124 can utilize one or more pattern recognition algorithms, each of which analyze the extracted features or a subset of the extracted features to assign a continuous or categorical parameter to the user. In one example, the assigned parameter can represent a predicted "relapse" of the user, that is, a predicted decrease in cognitive function, increase stress, increased cravings, pain, or depression, to an extent that will materially affect chances of substance use. In this example, sleep, activity data, and physiological data can be used along with results from a cognitive assessment and behavioral reporting applications to provide a continuous index representing the degree of changes of relapse by the user. It will be appreciated, however, that additional or alternative features can be used in the analysis and that the index can be replaced with a categorical classification (e.g., "near baseline", "reduced", "impaired") in some implementations. In another example, the predictive model 124 can be used to provide an index representing an internal marker of brain body balance, homeostasis, resilience and wellness. In yet another example, the predictive model 124 can be used to provide an index representing a measure of homeostasis for the user or to predict levels of the autonomic nervous system tone Where multiple classification or regression models are used, an arbitration element can be utilized to provide a coherent result from the plurality of models. The training process of a given classifier will vary with its implementation, but training generally involves a statistical aggregation of training data into one or more parameters associated with the output class. The training process can be accomplished on a remote system and/or on the local device or wearable, app. The training process can be achieved in a federated or non-federated fashion. For rule-based models, such as decision trees, domain knowledge, for example, as provided by one or more human experts, can be used in place of or to supplement training data in selecting rules for classifying a user using the extracted features. Any of a variety of techniques can be utilized for the classification algorithm, including support vector machines, regression models, self-organized maps, fuzzy logic systems, data fusion processes, boosting and bagging methods, rule-based systems, or artificial neural networks.

Federated learning (aka collaborative learning) is a machine learning technique that trains an algorithm across multiple decentralized edge devices or servers holding local data samples, without exchanging their data samples. This approach stands in contrast to traditional centralized machine learning techniques where all data samples are uploaded to one server, as well as to more classical decentralized approaches which assume that local data samples are identically distributed. Federated learning enables multiple actors to build a common, robust machine learning model without sharing data, thus addressing critical issues such as data privacy, data security, data access rights, and access to heterogeneous data. Its applications are spread over a number of industries including defense, telecommunications, IoT, or pharmaceutics.

For example, an SVM classifier can utilize a plurality of functions, referred to as hyperplanes, to conceptually divide boundaries in the N-dimensional feature space, where each of the N dimensions represents one associated feature of the feature vector. The boundaries define a range of feature values associated with each class. Accordingly, an output class and an associated confidence value can be determined for a given input feature vector according to its position in feature space relative to the boundaries. In one implementation, the SVM can be implemented via a kernel method using a linear or non-linear kernel.

An ANN classifier comprises a plurality of nodes having a plurality of interconnections. The values from the feature vector are provided to a plurality of input nodes. The input nodes each provide these input values to layers of one or more intermediate nodes. A given intermediate node receives one or more output values from previous nodes. The received values are weighted according to a series of weights established during the training of the classifier. An intermediate node translates its received values into a single output according to a transfer function at the node. For example, the intermediate node can sum the received values and subject the sum to a binary step function. A final layer of nodes provides the confidence values for the output classes of the ANN, with each node having an associated value representing a confidence for one of the associated output classes of the classifier.

Many ANN classifiers are fully-connected and feedforward. A convolutional neural network, however, includes convolutional layers in which nodes from a previous layer are only connected to a subset of the nodes in the convolutional layer. Recurrent neural networks are a class of neural networks in which connections between nodes form a directed graph along a temporal sequence. Unlike a feedforward network, recurrent neural networks can incorporate feedback from states caused by earlier inputs, such that an output of the recurrent neural network for a given input can be a function of not only the input but one or more previous inputs. As an example, Long Short-Term Memory (LSTM) networks are a modified version of recurrent neural networks, which makes it easier to remember past data in memory.

A rule-based classifier applies a set of logical rules to the extracted features to select an output class. Generally, the rules are applied in order, with the logical result at each step influencing the analysis at later steps. The specific rules and their sequence can be determined from any or all of training data, analogical reasoning from previous cases, or existing domain knowledge. One example of a rule-based classifier is a decision tree algorithm, in which the values of features in a feature set are compared to corresponding threshold in a hierarchical tree structure to select a class for the feature vector. A random forest classifier is a modification of the decision tree algorithm using a bootstrap aggregating, or "bagging" approach. In this approach, multiple decision trees are trained on random samples of the training set, and an average (e.g., mean, median, or mode) result across the plurality of decision trees is returned. For a classification task, the result from each tree would be categorical, and thus a modal outcome can be used.

In one implementation, the predictive model 124 can include a constituent model that predicts future values for craving-related parameters, such as a convolutional neural network that is provided with one or more two-dimensional arrays of wavelet transform coefficients as an input. The wavelet coefficients detect not only changes in time, but also in temporal patterns, and can thus reflect changes in the ordinary biological rhythms of the user. In one implementation, the craving-related parameters predicted by the constituent models can include measured parameters such as heart rate, temperature, and heart rate variability as well as self-report questions such as encountering trigger, feeling depressed, or increased life stress. It will be appreciated that a given constituent model can use data in addition to the wavelet coefficients, such as other measured features and user data 126 to provide these predictions.

The output of the predictive model 124 can be a categorical parameter representing a status of the user, such as "increased craving" or "decreased craving", "relapse" or "not relapse." A categorical parameter can also represent ranges of likelihoods for a current or predicted status. In another implementation, the output of the predictive model 124 can be a continuous parameter, such as a likelihood of a predicted or current status. In one example, the predictive model 124 can include one or more constituent models that predict a value for a craving-related parameter at a future time. For example, a given model can predict a physiological or behavior state for a user at a future time based on received data from the feature extractor 122 and stored user data 126. These predicted values can be provided to a user or utilized as inputs to additional models to predict a status of the user at the future time. In one example, the predictive model 124 includes a plurality of convolutional neural networks, each configured to predict a future value for a craving-related parameter, with the predicted values from the plurality of convolutional neural networks used to predict a future status of the user.

Figure 7:
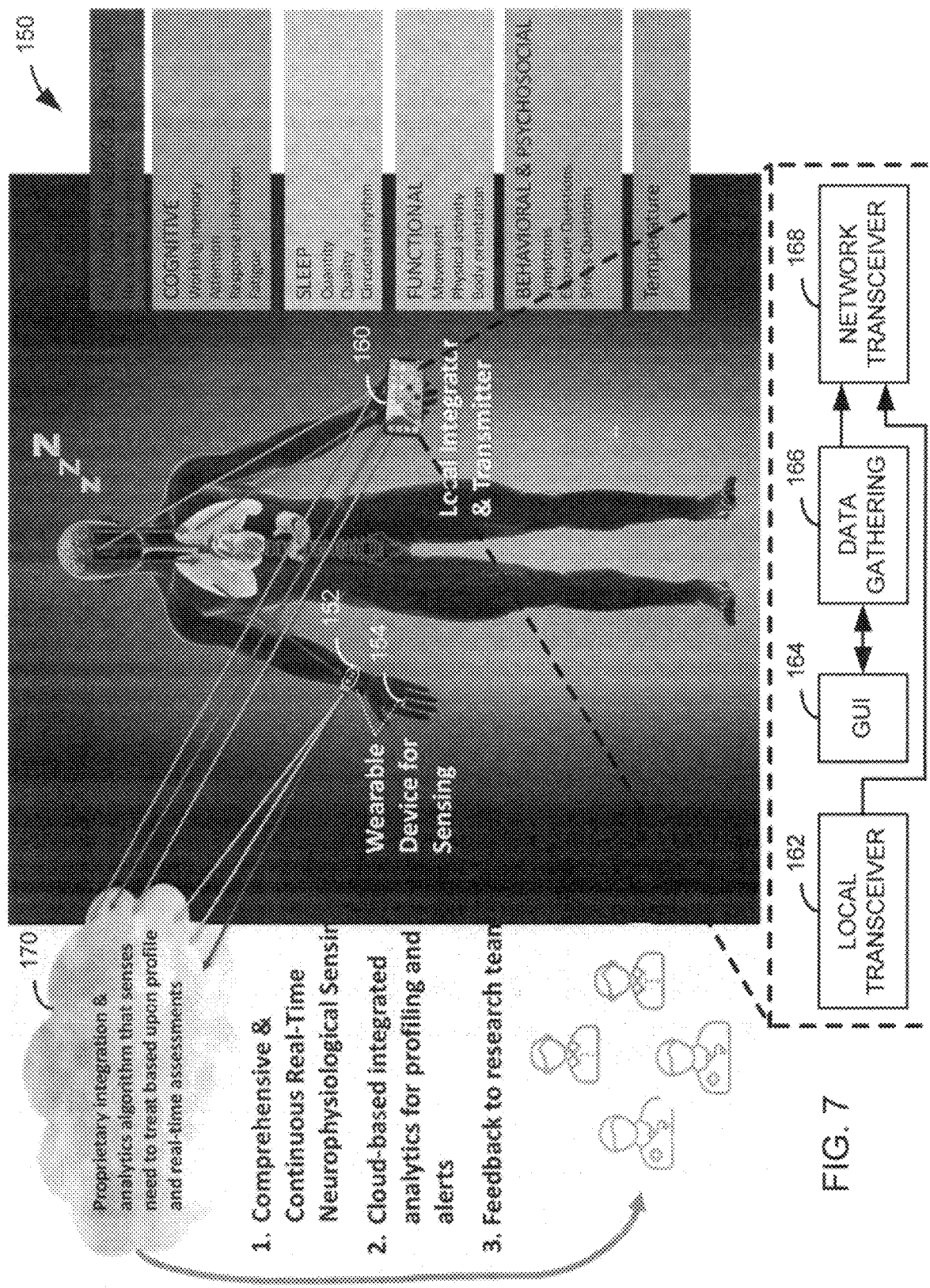
FIG. 7 is a schematic illustration of FIG. 5 using a plurality of portable monitoring devices.

FIG. 7 is a schematic example 150 of the system of FIG. 5 using a plurality of portable monitoring devices 152, 154, and 160. In the illustrated implementation, the first and second portable monitoring devices 152 and 154 are wearable devices, worn on the wrist and finger, respectively. Craving-relevant parameters monitored by the first and second portable monitoring devices 152 and 154 can include, for example, heart rate, heart rate variability, metrics of sleep quality, biological rhythm variations, metrics of sleep quantity, physical activity of the user, body orientation, movement, arterial blood pressure, respiratory rate, peripheral arterial oxyhemoglobin saturation, as measured by pulse oximetry, maximum oxygen consumption, temperature, and temperature variation. Wearable devices, as used herein, can include any wearable items implemented with appropriate sensors, including watches, wristbands, rings, headbands, headbands, and other wearable items that can maintain sensors in an appropriate position for monitoring the wellness-relevant parameters. It will be appreciated that a given wearable device 152 and 154 can monitor many of these parameters with great frequency (e.g., every five minutes) allowing for a detailed time series of data to be generated.

The system 150 can further include a mobile device 160 that communicates with the first and second portable monitoring devices 152 and 154 via a local transceiver 162. The mobile device 160 can also include a graphical user interface 164 that allows a user to interact with one or more data gathering applications 166 stored at the base unit. One example of a possible data gathering applications can include a cognitive assessment application that tests various measures of cognitive function. These can include working memory, attention, and response inhibition, fatigue, cognition. Further, these metrics can be compared to an established baseline to estimate a measure of fatigue for the user. Another data gathering application can include a questionnaire application that allows the user to self-report craving, mood, mental, physical, and emotional states, and stress.

The mobile device 160 further comprises a network transceiver 168 via which the system 150 communicates with a remote server 170 via a local area network or Internet connection. In this example, the remote server 170 includes a predictive model implemented as a recurrent neural network, specifically a network with a long short-term memory architecture. In this example, wellness-relevant parameters from the wearable devices 152 and 154, in combination with questionnaire responses and cognitive assessment, can be provided to the predictive model as time series along with other relevant data. An output of the model is an index representing craving and relapse risk posed to the user.

It will be appreciated that data can be collected from a plurality of users who may be socially connected, for example, as family, sponsor, coworkers, or friends. Social connections between users can be self-reported or derived from self-reported data, or, in one example, determined through analysis of location history from the mobile devices of monitored users. The use of location data or proximity sensors, which detect portable monitoring devices associated with other users within a threshold distance, might allow for instances of frequent spatial proximity that are not deliberate social contact (e.g., sharing a common vehicle for public transportation.) In one example, Bluetooth or similar short-range communication between mobile devices carried by users can be used to determine that users have been spatially proximate. An index indicating susceptibility or contraction to a known substance supply location could be used as part of a predictor for other, connected individuals. This data could also be used to predict locations at which illegal substances can be bought or used, allowing for an artificial intelligence driven smart location. It will be appreciated that information gathered from users will be stored in encrypted form and shared only after removal of personally identifying data to preserve users' privacy.

In one example, a high traffic location, such as a treatment clinics or support group meeting areas could have a number of Bluetooth beacons at known locations. As users pass the beacons, the Bluetooth transceiver in their mobile device will interact with the beacon, with an identifier for the user and a time stored for each interaction. These values, as well as other location and proximity information collected by the application, can be employed for determining the risk of relapse associated with various locations. A similar process can be performed using geolocation data collected by a GPS receiver, with users passing through a geofenced region associated with a given location recorded or the presence of drug seeking or treatment locations through a dynamic geofence associated with each device recorded.

Location data from user devices and/or designed Bluetooth beacons can be used to generate a mapping of relapse risk across a region of interest. In one example, the presence of user who reports increased craving or relapse associated with a given illegal substance via one of the data gathering applications 166 can be assigned to a given location. In another example, both users with reported relapse and users who are predicted to be have increased craving from the predictive model 124 can be used to generate the risk score. In one implementation, the contribution to the risk score for users who are predicted to have increased craving can be weighted according to a probability or confidence value associated with the prediction of being near a resent relapse user.

The map can be adjusted to show a symbol, color, or other indicator of relapse risk or area to seek support and a risk score can be generated. This risk score based on location can be individualized to specific users based on data they input for area they frequently use or buy substance at or areas where they go for support groups and therapy. The risk score can represent a total number of relapse reported at that location, a number of substance related arrests reported at that location over a defined window of time, either in total or over a defined window of time divided by an area of the location to generate a value representing a density of risk in that location. The risk score for each location can be shown on the map.

In one implementation, the thresholds used to define each category can be defined according to the characteristics of the user, for example, as represented by the user data 126, or by a determination of the user's resilience to craving as determined at the predicted model 124. For example, if a user is in a high-risk category for craving and relapse, the threshold can be lowered to represent the user's increased risk of relapse. Similarly, if the user's resilience is determined to be lowered at a given time, the thresholds can be temporarily lowered to represent the user's decreased ability to resist craving. Accordingly, the map can not only be personalized to a given user, but can be adjusted to represent the risk to the user at a specific time.

Figure 6:
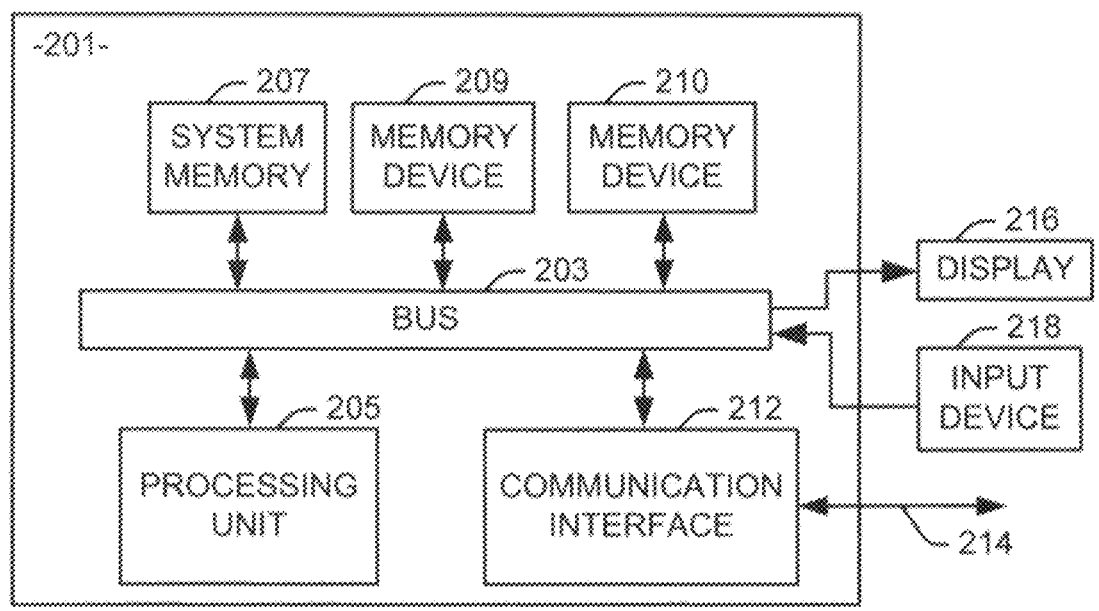
FIG. 6 is a schematic block diagram illustrating an exemplary system of hardware components.

FIG. 6 is a schematic block diagram illustrating an exemplary system 201 of hardware components capable of implementing examples of the systems and methods disclosed herein. The system 201 can include various systems and subsystems. The system 201 can be a personal computer, a laptop computer, a workstation, a computer system, an appliance, an application-specific integrated circuit (ASIC), a server, a server BladeCenter, a server farm, etc.

The system 201 can include a system bus 203, a processing unit 205, a system memory 207, memory devices 209 and 210, a communication interface 212 (e.g., a network interface), a communication link 214, a display 216 (e.g., a video screen), and an input device 218 (e.g., a keyboard, touch screen, and/or a mouse). The system bus 203 can be in communication with the processing unit 205 and the system memory 207. The additional memory devices 209 and 210, such as a hard disk drive, server, standalone database, or other non-volatile memory, can also be in communication with the system bus 203. The system bus 203 interconnects the processing unit 205, the memory devices 207, 208, 210, the communication interface 212, the display 216, and the input device 218. In some examples, the system bus 203 also interconnects an additional port (not shown), such as a universal serial bus (USB) port.

The processing unit 205 can be a computing device and can include an application-specific integrated circuit (ASIC). The processing unit 205 executes a set of instructions to implement the operations of examples disclosed herein. The processing unit can include a processing core.

The additional memory devices 207, 209, and 210 can store data, programs, instructions, database queries in text or compiled form, and any other information that may be needed to operate a computer. The memories 207, 209 and 210 can be implemented as computer-readable media (integrated or removable), such as a memory card, disk drive, compact disk (CD), or server accessible over a network. In certain examples, the memories 207, 209 and 210 can comprise text, images, video, and/or audio, portions of which can be available in formats comprehensible to human beings.

Additionally or alternatively, the system 201 can access an external data source or query source through the communication interface 212, which can communicate with the system bus 203 and the communication link 214.

In operation, the system 201 can be used to implement one or more parts of a system for monitoring a wellness of a user in accordance with the present invention. Computer executable logic for implementing the monitoring system resides on one or more of the system memory 207, and the memory devices 209 and 210 in accordance with certain examples. The processing unit 205 executes one or more computer executable instructions originating from the system memory 207 and the memory devices 209 and 210. The term "computer readable medium" as used herein refers to a medium that participates in providing instructions to the processing unit 205 for execution. This medium may be distributed across multiple discrete assemblies all operatively connected to a common processor or set of related processors. Specific details are given in the above description to provide a thorough understanding of the embodiments. However, it is understood that the embodiments can be practiced without these specific details. For example, physical components can be shown in block diagrams in order not to obscure the embodiments in unnecessary detail. In other instances, well-known circuits, processes, algorithms, structures, and techniques can be shown without unnecessary detail in order to avoid obscuring the embodiments.

Implementation of the techniques, blocks, steps and means described above can be done in various ways. For example, these techniques, blocks, steps and means can be implemented in hardware, software, or a combination thereof. For a hardware implementation, the processing units can be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above, and/or a combination thereof.

Also, it is noted that the embodiments can be described as a process which is depicted as a flowchart, a flow diagram, a data flow diagram, a structure diagram, or a block diagram. Although a flowchart can describe the operations as a sequential process, many of the operations can be performed in parallel or concurrently. In addition, the order of the operations can be re-arranged. A process is terminated when its operations are completed, but could have additional steps not included in the figure. A process can correspond to a method, a function, a procedure, a subroutine, a subprogram, etc. When a process corresponds to a function, its termination corresponds to a return of the function to the calling function or the main function.

Furthermore, embodiments can be implemented by hardware, software, scripting languages, firmware, middleware, microcode, hardware description languages, and/or any combination thereof. When implemented in software, firmware, middleware, scripting language, and/or microcode, the program code or code segments to perform the necessary tasks can be stored in a machine readable medium such as a storage medium. A code segment or machine-executable instruction can represent a procedure, a function, a subprogram, a program, a routine, a subroutine, a module, a software package, a script, a class, or any combination of instructions, data structures, and/or program statements. A code segment can be coupled to another code segment or a hardware circuit by passing and/or receiving information, data, arguments, parameters, and/or memory contents. Information, arguments, parameters, data, etc. can be passed, forwarded, or transmitted via any suitable means including memory sharing, message passing, ticket passing, network transmission, etc.

For a firmware and/or software implementation, the methodologies can be implemented with modules (e.g., procedures, functions, and so on) that perform the functions described herein. Any machine-readable medium tangibly embodying instructions can be used in implementing the methodologies described herein. For example, software codes can be stored in a memory. Memory can be implemented within the processor or external to the processor. As used herein the term "memory" refers to any type of long term, short term, volatile, nonvolatile, or other storage medium and is not to be limited to any particular type of memory or number of memories, or type of media upon which memory is stored.

Moreover, as disclosed herein, the term "storage medium" can represent one or more memories for storing data, including read only memory (ROM), random access memory (RAM), magnetic RAM, core memory, magnetic disk storage mediums, optical storage mediums, flash memory devices and/or other machine readable mediums for storing information. The term "machine-readable medium" includes, but is not limited to portable or fixed storage devices, optical storage devices, wireless channels, and/or various other storage mediums capable of storing that contain or carry instruction(s) and/or data.

Addiction includes addiction to an addictive behavior or an addictive chemical substance Non-limiting examples of addiction to an addictive behavior include addiction to gambling, food, sex, shopping, sports and physical exercise, video gaming, media use, pathological working, and compulsive criminal behavior. Non-limiting examples of addiction to an addictive chemical substance include addiction to nicotine; alcohol; *cannabis*; painkillers such as, for example, opioids; cocaine; heroin; benzodiazepines; stimulants such as, for example, amphetamines including methamphetamine and dextroamphetamine, and methylphenidate; inhalants such as, for example, gasoline, household cleaning products, and aerosols; and sedatives/hypnotics such as, for example, barbiturates, zolpidem tartrate, and eszopiclone.

EXAMPLE

A 25 year old male subject was diagnosed with opioid use disorder and cocaine use disorder. His age of first use of heroin is 14 years of age, and first use of cocaine 22 years of age. He has been using heroin regularly (defined as >3 days per week) for the past 9 years and using cocaine regularly for the last 2 years. Although his weekly use of heroin and cocaine would fluctuate based on access and availability, he reported typically using both heroin and cocaine three to four times per week over the past month. He has been receiving treatment intermittently since 2014 in the Intensive Outpatient Program and in the MAT program referred to as the Comprehensive Opioid Addiction Treatment (COAT) program at the WVU School of Medicine's Chestnut Ridge Center. At the time of study participation, the subject was enrolled in the COAT program, which utilizes a multidisciplinary and multimodal approach including behavioral intervention (both group and individual therapy) and buprenorphine/naloxone maintenance. He also received treatment in two 28-day residential treatment programs over the last 4 years. During all of these treatments, he has had frequent relapses, not being able to remain drug abstinent for longer than approximately 50 days, and no longer than a few days of abstinence over the past six months. This individual's substance use has led to several physical, psychosocial, and legal complications, including infectious disease—related abscess, drug overdose, car accidents, depression, anxiety, impaired interpersonal relationships, job loss, and multiple arrests (with one episode of incarceration).

Procedures

The procedures conducted as part of this study were approved by the WVU Institutional Review Board. The subject participated in a screening session after providing written informed consent, and he met the approved inclusion/exclusion criteria to participate in this study. Inclusion criteria included the following: (1) actively enrolled in the COAT Program; (b) meet Diagnostic and Statistical Manual of Mental Disorders, fifth edition (DSM-V) criteria for a primary OUD and comorbid SUD assessed via structured clinical interview; (c) 18-60 years of age; (d) abstinent from opioids (other than prescribed buprenorphine/naloxone) and illicit substances other than marijuana at the time of the enrollment (confirmed via urine drug screen); (e) willing to practice contraception to avoid pregnancy the duration of the study; (f) able to provide written informed consent and to comply with study procedures. Exclusion criteria included the following: (a) Medical conditions that preclude repetitive transcranial magnetic stimulation (rTMS); (b) DSM-V criteria for major psychiatric illness; (c) major cognitive disorder; (d) pregnancy; (e) positive responses to the Transcranial Magnetic Stimulation Adult Safety Screen; (f) taking any medications that are a strong potential hazard for rTMS; (g) intracranial metallic objects; (h) uncorrected visual acuity problems; (i) clinically significant electrocardiogram abnormalities; (j) unwilling to abstain from proscribed drugs; (k) suicidal ideation; (l) prior rTMS treatment; and (m) other mental or physical conditions that, in the principal investigator's opinion, would be inappropriate for study participation.

Craving was assessed at baseline, at which time the subject was asked to rate his cravings for heroin, cocaine, and other substances, via a 100-point visual analog scale (VAS) where 100 represented maximum craving and 0 represented no craving. After this initial craving assessment, the patient was then exposed to heroin and other substance-related cues (e.g., images of drugs, paraphernalia, people using drugs), which were presented on a laptop for 10 minutes, followed by an assessment of craving (VAS) to determine changes in craving following cue exposure. rTMS was then applied unilaterally over the left dorsolateral prefrontal cortex (DLPFC) during seven sessions across a 3-week time course using a TMS device. The DLPFC was identified using the "5 cm" method, which involves stimulating the motor cortex, observing motor evoked potentials in the contralateral hand, and then measuring 5 cm anterior from this position along a parasaggital line (George et al., 1995; Pascual-Leone, Rubio, Pallardo, & Catala, 1996). Cue exposure continued throughout the rTMS administration and for 10 minutes after the completion of the rTMS sessions. Craving was assessed immediately after rTMS administration and again at 5 and 10 minutes post-completion of the rTMS sessions.

Results

Over the course of the study, all procedures were well tolerated with no adverse events reported by the subject (assessed before, during, and following TMS sessions). Across the seven sessions, exposure to the drug-related cues resulted in an increase in craving for heroin (average: 41.4 precue exposure vs. 68.6 postcue exposure) and cocaine (41.4 vs. 71.4). Following the 10 minute rTMS administration, craving ratings for heroin decreased from 68.6 to 27.1 immediately following the completion of rTMS with an even further decrease 5 min (18.6) and 10 min (14.3) post-rTMS completion on average across the seven sessions. Craving ratings for cocaine decreased from 71.4 to 25.7 immediately following the completion of rTMS sessions with an even further decrease 5 min (18.6) and 10 min (12.9) post-rTMS completion on average across the seven sessions.

CONCLUSIONS

Although this is a single case, these findings demonstrate that further investigation of rTMS as an augmentation strategy with comprehensive MAT for OUD and polysubstance use disorder is warranted. There are two primary findings which became apparent from this case. First, cue-induced craving could be elicited via the presentation of substance related cues with increases of heroin and cocaine craving by approximately 57% to 59% in comparison with his baseline, precue exposure craving ratings. Following 10 minutes of rTMS applied unilaterally over the left DLPFC, there was on average an approximate 60% to 80% decrease in heroin craving and 63% to 82% decrease in cocaine craving across the seven sessions. The decreases in craving following rTMS administration, at which time the participant had continued exposure to the drug related cues, were approximately 36% to 68% below his initial precue exposure craving rating. This demonstrates that cue-induced craving, at least in this particular case, could be extinguished by rTMS. This is of importance given that cues (such as images of drugs, situations when drugs are used, people who are affiliated with an individual's drug use, etc.) are associated with continued drug taking and relapse. By extinguishing cue induced craving, the probability of an individual relapsing in the context of increased craving elicited by drug related cues will hopefully then be reduced. Although the cues presented to the subject clearly elicited a craving response, this must be interpreted in the context of the environment (clinic setting) and potentially reflect a response less robust than that which would be elicited in a naturalistic setting. As such, to maximize the craving response and attempt to approximate that response which would be elicited in a naturalistic setting, tailoring the cue presentation to each individual is one possible method. For example, selecting cues as proximal to the subject's characteristics (e.g., age, gender, ethnicity, preferred substances and route of substance administration, etc.) proved to be beneficial in eliciting a craving response which he reported as being relatively comparable with his craving outside the clinic in a more naturalistic setting.

When asked qualitatively about why he felt his craving decreased during and after the rTMS sessions, the subject reported that the images had more of an "aversive effect" as opposed to when he viewed the cues in the absence of the rTMS. He reported that during and after the rTMS administration sessions, he reflected more about the negative impact his substance use has had on his life, specifically how it has led to issues within the legal system, caused friction within his family, and has interfered with his daily functioning (e.g., maintaining employment). Without wishing to be bound by theory, this may reflect changes in the targeted region where the rTMS was administered. Given that the left DLPFC is implicated in inhibition and decision-making, the subject's report that the cues made him consider the negative impact substance use has had on his life may suggest increased activity in these decision-making networks. Of importance, this subject remained entirely abstinent for approximately one month following the completion of the final rTMS session, a considerable improvement given that his previous lengths of abstinence over the prior six months were typically no longer than a few days.

Modifying the duration, frequency, and intensity of treatment parameters (e.g., from thrice-weekly over 3 weeks to 5 days per week over 6 weeks) may be considered. Other forms of TMS, such as intermittent and continuous theta burst stimulation may also be used. In addition, other areas of the brain which are also involved in reward neurocircuitry, such as the medial prefrontal cortex, can be targeted.

Each of the disclosed aspects and embodiments of the present disclosure may be considered individually or in combination with other aspects, embodiments, and variations of the disclosure. Further, while certain features of embodiments and aspects of the present disclosure may be shown in only certain figures or otherwise described in the certain parts of the disclosure, such features can be incorporated into other embodiments and aspects shown in other figures or other parts of the disclosure. Along the same lines, certain features of embodiments and aspects of the present disclosure that are shown in certain figures or otherwise described in certain parts of the disclosure can be optional or deleted from such embodiments and aspects. Additionally, when describing a range, all points within that range are included in this disclosure. Further, unless otherwise specified, none of the steps of the methods of the present disclosure are confined to any particular order of performance. Furthermore, all references cited herein are incorporated by reference in their entirety.

What is claimed is:

1. A method of improving addiction to an addictive behavior or addictive chemical substance in a patient in need thereof comprising:
    obtaining a measurement of the patient's baseline craving level for the addictive behavior or addictive chemical substance;
    providing the patient exposure to a cue associated with the addictive behavior or addictive chemical substance;
    obtaining a subsequent measurement of the patient's resultant craving level for the addictive behavior or addictive chemical substance during or after exposure to the cue; and
    delivering a neuromodulation signal comprising a focused ultrasound signal, a transcranial magnetic stimulation signal, and/or a deep brain stimulation signal to the patient based on a comparison of the baseline craving level and the resultant craving level to improve the patient's addiction.

2. The method of claim 1, wherein delivering the neuromodulation signal comprises delivering the neuromodulation signal to a neural target site of the patient's brain reward circuitry.

3. The method of claim 2, wherein the neuromodulation signal is a focused ultrasound signal.

4. The method of claim 2, wherein the neuromodulation signal is a transcranial magnetic stimulation signal.

5. The method of claim 2, wherein the neuromodulation signal is a deep brain stimulation signal.

6. The method of claim 1, wherein delivering the neuromodulation signal comprises delivering the neuromodulation signal to the patient upon a determination that the resultant craving level increases above the patient's baseline craving level.

7. The method of claim 1, wherein delivering the neuromodulation signal comprises providing or adjusting delivery of the neuromodulation signal to the patient upon a determination that the resultant craving level increases above the patient's baseline craving level, wherein adjusting delivery of the neuromodulation signal comprises increasing the frequency, duration, intensity, sonication duration, pulse width, sonication dose, number of sonication elements, or a combination thereof of the neuromodulation signal.

8. The method of claim 1, wherein delivering the neuromodulation signal comprises providing or adjusting delivery of the neuromodulation signal to the patient upon a determination that the resultant craving level remains substantially the same or decreases compared to the patient's baseline craving level, wherein adjusting delivery of the neuromodulation signal comprises decreasing the frequency, duration, intensity, or a combination thereof of the neuromodulation signal or maintaining the same frequency, duration, intensity or a combination thereof of the neuromodulation signal.

9. The method of claim 1, wherein the cue is a visual cue, an auditory cue, a tactile cue, an olfactory cue, or combinations thereof.

10. The method of claim 1, wherein obtaining a measurement of the patient's baseline craving level is obtaining a measurement before or during delivery of the neuromodulation signal.

11. A method of improving addiction to an addictive behavior or addictive chemical substance in a patient in need thereof comprising:
    obtaining a measurement of a baseline value of a cognitive, psychosocial or behavioral parameter relevant to the patient's addiction to the addictive behavior or addictive chemical substance of the patient;
    providing the patient exposure to a cue associated with the addictive behavior or addictive chemical substance;
    obtaining a subsequent measurement of a resultant value of the cognitive, psychosocial or behavioral parameter relevant to the patient's addiction to the addictive behavior or addictive chemical substance of the patient during or after exposure to the cue; and
    delivering a neuromodulation signal comprising a focused ultrasound signal, a transcranial magnetic stimulation signal, and/or a deep brain stimulation signal to the patient based on a comparison of the baseline value and the resultant value to improve the patient's addiction.

12. The method of claim 11, wherein delivering the neuromodulation signal comprises delivering a focused ultrasound signal, a transcranial magnetic stimulation signal, and/or a deep brain stimulation signal to the patient upon a determination that the resultant value increases above the baseline value.

13. The method of claim 11, wherein obtaining a measurement of the resultant value during or after exposure to the cue comprises obtaining the measurement during exposure to the cue and within ten minutes after exposure to the cue.

14. The method of claim 11, wherein the physiological parameter is a response at least partially regulated by the autonomic nervous system.

15. The method of claim 11, wherein obtaining a measurement of the patient's baseline value of the cognitive, psychosocial or behavior parameter is obtaining a measurement before or during delivery of the neuromodulation signal.

16. A method of monitoring addiction to an addictive behavior or addictive chemical substance in a patient in need thereof comprising:
    obtaining a measurement of a baseline value of a physiological parameter of the patient or a baseline craving level of the patient;

providing the patient exposure to a cue associated with the addictive behavior or addictive chemical substance;

obtaining a measurement of a resultant value of the physiological parameter or a resultant craving level during or after exposure to the cue;

obtaining a comparison of the resultant value of the physiological parameter and the baseline value of the physiological parameter or a comparison of the resultant craving level and the baseline craving level;

delivering a neuromodulation signal comprising a focused ultrasound signal, a transcranial magnetic stimulation signal, and/or a deep brain stimulation signal to the patient before based on a comparison of the baseline value of the physiological parameter and the resultant value of the physiological parameter or a comparison of the baseline craving level of the patient and the resultant craving level of the patient;

providing a notification to the patient or a third party based on the comparison of the baseline value of the physiological parameter and the resultant value of the physiological parameter or the baseline craving level and the resultant craving level to monitor the patient's addiction.

17. The method of claim 16, wherein providing a notification comprises providing a notification to the patient or the third party upon a determination that the resultant value increases above the baseline value or the resultant craving level increases above the baseline craving level.

18. The method of claim 16, wherein obtaining a measurement of the patient's baseline value of the physiological parameter or of the patient's baseline craving level is obtaining a measurement before or during delivery of the neuromodulation signal.

* * * * *